(12) United States Patent
Tavares et al.

(10) Patent No.: US 7,261,759 B2
(45) Date of Patent: Aug. 28, 2007

(54) POWDER METAL MIXTURE INCLUDING MICRONIZED STARCH

(75) Inventors: Bruce Anthony Tavares, Hartland, WI (US); Bart Jerome Nelson, Johnsonburg, PA (US)

(73) Assignee: React-NTI, LLC, Lino Lakes, MN (US)

( * ) Notice: Subject to any disclaimer, the term of this patent is extended or adjusted under 35 U.S.C. 154(b) by 606 days.

(21) Appl. No.: 10/758,031

(22) Filed: Jan. 14, 2004

(65) Prior Publication Data

US 2004/0144206 A1 Jul. 29, 2004

Related U.S. Application Data

(63) Continuation-in-part of application No. 10/229,452, filed on Aug. 28, 2002, now Pat. No. 6,683,031, which is a continuation-in-part of application No. 09/861,842, filed on May 21, 2001, now Pat. No. 6,506,712.

(51) Int. Cl.
*B22F 1/00* (2006.01)
*B22F 3/02* (2006.01)
*C08L 3/00* (2006.01)

(52) U.S. Cl. .............. 75/252; 419/62; 419/66; 524/35; 524/47

(58) Field of Classification Search .......... 75/252, 75/246; 524/47, 35; 419/62, 66
See application file for complete search history.

(56) References Cited

U.S. PATENT DOCUMENTS

| | | | | |
|---|---|---|---|---|
| 3,307,927 A | * | 3/1967 | Muschenborn et al. | 75/766 |
| 3,481,714 A | * | 12/1969 | Harrington et al. | 75/246 |
| 4,053,379 A | * | 10/1977 | Fox et al. | 536/111 |
| 4,288,913 A | * | 9/1981 | Parsen et al. | 29/623.5 |
| 4,402,736 A | * | 9/1983 | Graham | 75/321 |
| 4,483,905 A | * | 11/1984 | Engstrom | 428/570 |
| 5,480,469 A | | 1/1996 | Storstrom et al. | |
| 5,568,652 A | * | 10/1996 | Wu | 264/434 |
| 6,413,919 B2 | | 7/2002 | Vidarsson | |
| 6,511,945 B1 | | 1/2003 | Ramstedt | |
| 6,573,225 B1 | | 6/2003 | Vidarsson et al. | |

FOREIGN PATENT DOCUMENTS

| | | |
|---|---|---|
| EP | 1179607 A | 2/2002 |
| GB | 1 162 702 A | 8/1969 |
| JP | 11 302302 A | 2/1999 |
| WO | 9205290 * | 4/1992 |

* cited by examiner

*Primary Examiner*—Roy King
*Assistant Examiner*—Ngoclan T. Mai
(74) *Attorney, Agent, or Firm*—Alfred D. Lobo

(57) ABSTRACT

A powder metal mixture comprises a lubricant powder conventionally used to produce powder metal parts in combination with a modified lubricant. A lubricant conventionally used to compact and sinter a chosen powder metal mixture is modified by adding to it starch particles smaller than the average metal particle, and optionally, micronized cellulose fibers in so small an amount that the modified lubricant is present in an amount less than 2% by weight of the mixture. The Hall apparent density and the Hall flow rate of a powder metal mixture made with the modified lubricant of starch or (starch+fibers) remains within the ranges deemed desirable for production of compacted powder metal parts. Using the modified lubricant in lieu of the conventional lubricant increases green strength of a part made by compacting the mixture and improves dimensional conformance.

16 Claims, No Drawings

POWDER METAL MIXTURE INCLUDING MICRONIZED STARCH

CROSS REFERENCE TO RELATED APPLICATIONS

This patent application is a continuation-in-part application of Ser. No. 10/229,452 filed 28 Aug. 2002 now U.S. Pat. No. 6,683,031, which is a continuation-in-part application of Ser. No. 09/861,842 filed 21 May 2001, issued as U.S. Pat. No. 6,506,712 ("'712 patent") on 14 Jan. 2003.

FIELD OF THE INVENTION

The present invention relates to a novel powder metal mixture in which a particulate ferrous metal powder in combination with a binder and lubricant is conventionally molded into an article of arbitrary shape and size having sufficient green strength to be ejected from the die in which the article is molded without scoring the die and without generating so much heat as to blister lubricant out of the compacted part.

BACKGROUND OF THE INVENTION

The demands of mass production of metal parts for appliances, vehicles and machines of all types has driven the technology of powder metallurgy ever since it was discovered that a mixture of the appropriate finely divided metal particles in the form of a powder, mixed with a binder and lubricant, each also in finely divided form, could be compacted and sintered to yield an article of arbitrary shape and size. In the art, "powder metal mixture" refers to a mass of particles each of which is less than 150 µm (micrometers or microns) in average equivalent diameter ("avg. equiv. dia."), preferably its largest dimension, the metal particles typically being largest, preferably having an avg. equiv. dia. of less than 75 µm, the smallest metal particles having an avg. equiv. dia. of about 25 µm, and the non-metallic additives typically having an avg. equiv. dia. smaller than that of the metal particles, typically less than 50 µm. Depending upon the physical properties demanded of the sintered, or sintered and heat treated, ferrous article, a wide array of powder additives are added. The most common of such additives are a lubricant and/or graphite, followed by metals such as nickel, copper, molybdenum, manganese, chromium, cobalt and/or an organometal or metal compounds such as sulfides, phosphides, and the like which become alloyed with the powder metal when sintered and/or heat treated.

The term "powder metal mixture" in this invention refers to a mixture of ferrous metal particles in which mixture the ferrous metal powder is present in an amount greater than 90 per cent, the remaining ingredients being additives such as a lubricant, optionally a binder which may be the same as the lubricant or different, and alloying ingredients such as graphite and metals, each present in an amount less than 2 per cent by weight (% by wt) of the total mixture including the powder.

The term "lubricant" refers to a powder of particles no dimension of which is more than about 100 µm, and typically having an avg. equiv. dia. in the range from about 5 µm to 25 µm; in this invention the lubricant is modified to consist essentially of a lubricant powder such as is conventionally used to make a compact mass of powder metal, blended with particulate starch having an avg. equiv. diam. length less than 150 µm, preferably less than 50 µm, optionally in combination with no more than an equal amount of micron-sized fragments cellulose fibers, like starch, a polysaccharide, provided that 90% of the fragments have a length less than the avg. equiv. dia. of the metal particles. Modification of a conventionally used powder metal lubricant with starch alone, for convenience and brevity, is referred to as "starchlube".

Because powder metal particles, like starch particles may be irregular in shape, the equivalent diameter of a particle refers to its diameter had it been a sphere of equal volume.

The cellulose fragments which may be mixed with starch particles are preferably much smaller than 50 µm and in a narrow size range, that is, at least 90% by wt are less than 10 µm in length, and the average length of all fragments is in the range from about 4-5 µm. The fragments are referred to as being "micronized" as they are conveniently obtained by feeding cellulose fibers in short lengths less than about 6.35 mm (0.25") to a commercially available jet classifying mill or "micronizer" such as a Model 30 Roto-Jet manufactured by Fluid Energy A1-Jet Company. Most preferably the cellulose fibers, such as cotton, hemp, manila, sisal, jute and the like, are first irradiated with enough radiation to alter their surface structure, preferably by exposing the fibers to electron beam radiation to receive a dosage, typically measured as kiloGrays (kGy), in a range equivalent to from about 30 to 100 MegaRads, as described in detail in the aforementioned '712 patent, the disclosure of which is incorporated by reference thereto as if fully set forth herein. Because, like starch particles, cellulose fragments have no notable lubricity they are together referred to as a "non-lubricant".

The overriding criterion for a practical powder mixture is its homogeneity without which there would be an unacceptable variance in composition of a compacted metal part, not only from part to part, but within a part itself. The term "part" is used interchangeably with the more formal term "article". Such homogeneity encompasses not only the distribution of particles within a mass of unit volume of powder but the bulk density (measured as "Hall apparent density") and flow characteristics (measured as "Hall flow rate") of the powder mixture. The apparent density is the mass of a unit volume of non-compacted powder. Hall apparent density is measured as set forth in ASTM B-212 (Metal Powder Industries Federation "MPIF" test method 04 in "Standard Test Methods for Metal Powders and Powder Metallurgical Products). The flow rate is quantified as the time required for a powder of standard weight to flow through a Hall flow meter. The Hall flow rate is dictated by ASTM B-213 (MPIF test method 03). A variation in bulk density and flow will result in a variation in the "fill", which is the amount of powder mixture filled in a die cavity before the mixture is compacted, and the dimensions of the compacted part. To a lesser extent, a lack of homogeneity is reflected in variations in green strength of a compacted part particularly in sensitive portions of the molded part, such as the teeth of a gear.

Mainly because adequate green strength is obtained by increasing compacting pressure, green strength as a serious problem attracts attention only in those instances where compaction, or molding pressure is already so high as to shorten the useful life of a die noticeably and/or a worrisome number of compacted parts are damaged when being ejected from the die, or being automatically conveyed to a sintering oven under conditions which cannot preclude the green compacts from being impacted, even if not forcefully.

Green strength is measured as pressure required to break an unsintered compact (a standard rectangular bar) as set forth in ASTM B-312 (MPIF test method 15).

Though the terms "binder" and "lubricant" are used as if to specify different functions in a powder metal blend to be compacted, in practice, the same function may be discharged by a single ingredient, though each function may be to a greater or lesser extent than when discharged by different highly specialized materials. In particular, ethylene-bis-stearamide ("EBS") is sometimes referred to as a "binder" though it may also function as a lubricant, and metal soaps and waxes are typically referred to as "lubricants" though they may also function as binders. The term "blend" refers to a ferrous metal powder including all ingredients essentially homogeneously dispersed and in condition to be compacted. By "ferrous" metal powder is meant one in which the metal particles contain predominantly the element iron (Fe), typically at least 75% Fe. The binder binds particles of graphite and alloying components to the surface of metal particles. The lubricant reduces friction generated when the powder is subjected to shear, or, stressed; thus, metal powder with lubricant particles flows more easily than without the lubricant; and, a powder mixture with lubricant added to the metal particles may be compacted in a die under pressure and, if the compact has sufficient green strength, ejected from the die with less wear and tear on the die parts.

Typically, the green article is then sintered. The strength of the sintered bar is measured as "transverse rupture strength" ("TRS") using a standard TRS fixture as described in ASTM B-528 (MPIF test method 41). If the TRS is satisfactory, the tensile strength will generally be satisfactory. Depending upon the composition of the mixture of powder metal and additives from which the article is molded, and its end use, it may be subjected to further processing steps such as sizing/coining, resintering, heat treating, and others.

Recognizing that the component powders of metal, binder and/or lubricant and one or more additional additives differ in size, density and shape, the problem of homogeneity is minimized by choosing particles of comparable size and shape and thoroughly mixing the various particles before using the powder mixture. In this framework, it is evident that any thought of mixing starch particles optionally with an organic fiber of vegetable material with the lubricant and metal particles, no matter how beneficial the non-lubricant might otherwise be, will be quickly dispelled.

Moreover, to date, starch particles have not been used as a lubricant or binder in a powder metal part, because starch, like cellulose and other polysaccharides would not be expected to have any measurable beneficial value for this purpose. Though both starch and cotton have similar chemical formulae, cellulose is a polymer of cellobiose and starch is a polymer of amylose. Each polymer is structurally different and the difference in structures results in greatly differing properties. For example, starches are generally edible by humans, while cellulose is not. Moreover, polycellobiose occurs naturally as fibers, while starch is particulate.

Addition of starch particles in an amount as little as 2% by wt of the total powder mixture, whether of a water-soluble starch or a water-insoluble starch, having an average diameter no smaller than 50 μm, though in the same size range as the avg. equiv. diam. of metal particles used in a compactable powder mixture, results in both unacceptable bulk or apparent density as well as flow characteristics, if the mixture is to be used in the mass production of compacted and sintered parts. The poor physical properties of a powder metal mixture containing starch particles 50 μm and larger is attributable to the volume the particles occupy and the irregularity of their individual shapes. Addition of starch particles smaller than 50 μm, referred to as "micronized starch", optionally in combination with micronized cotton fibers in a total amount as little as 2% by wt, no matter what their respective proportions, produces the same effects as with starch alone.

On the other hand, it is well recognized that the increased surface area contributed by the smaller particles in a powder mixture relative to the area contributed by the larger ones, impairs the "flowability" or flow characteristics of the powder mixture, resulting in a longer time required to fill a die and additional risk of non-homogeneity in compacted parts. Though such flowability is not a problem when compacting a dozen parts or so in a laboratory, the problem may be critical in a production facility where the number of parts which can be produced per unit time is a deciding factor.

Another serious problem which has loomed large in recent years is the extent of "dusting", particularly of graphite, and the harmful side effects of vaporizing zinc stearate, commonly used as a lubricant, during sintering. To cope with the latter problem, particularly having to clean sintering furnaces and their flues, the art is proliferated with disclosures of numerous other lubricants including waxes and metal soaps. To minimize or eliminate the use of zinc stearate, polyethylene oxide in combination with an oligomeric amide is disclosed in U.S. Pat. No. 6,511,945; and EBS or a polycarboxylic acid amide wax is used as a binder, but making a homogeneous powder mixture typically requires heating the wax to distribute it uniformly as a coating on the metal particles, as disclosed in U.S. Pat. No. 5,480,469 to Storstrom et al. and U.S. Pat. No 6,573,225 to Vidarsson et al. respectively. To improve lubrication, U.S. Pat. No. 6,413,919 uses a combination of two well-known lubricants, each effective in its own right, one a fatty acid mono- or bis-amide, e.g. EBS, the other a metal soap, e.g. zinc stearate, and relies upon processing the mixture to form a core of one lubricant coated with the other.

SUMMARY OF THE INVENTION

An article of arbitrary shape and size is provided which is molded from (i) a ferrous metal powder having an average particle size smaller than about 150 μm (30 mesh U.S. Standard Sieve Series) in combination with (ii) a particulate, flowable lubricant having an average particle size smaller than about 50 μm, preferably smaller than 30 μm, and with (iii) starch particles having an avg. equiv. diam. smaller than 50 μm, preferably in the range from about 1 μm to 50 μm, or (iv) the starch particles in combination with micronized cellulose fibers; the article is molded from a powder metal mixture in which the lubricant and starch particles are together present in an amount in the range from about 0.01% to less than 2% by wt, each preferably present in an amount less than 1% by wt of the mixture. About 90% by wt of the starch particles have an avg. equiv. diam. in the range from 5 to 50 μm; in the range from 5 to 40% by wt have an avg. equiv. diam. in the range from 2 to 20 μm, and from 1 to 20% by wt have an average equiv. diam. in the range from 1 to 10 μm, as measured in a Microtrac Standard Range Particle Analyzer.

Most preferred are starch particles in the aforementioned size range which have been irradiated with X-rays or gamma rays, preferably gammas, having an intensity sufficient to provide a dosage effective to modify at least the surface of the starch particles if not their chemical structure. Representative are particles of corn starch such as available from National Starch & Chemical Corp. as Purity® 21C which have received a dosage in the range from about 10 to 30 MegaRads, most preferably about 15 MegaRads from a Cobalt 60 gamma ray source. The dosage required for different starches will vary depending in large part upon their suitability without being irradiated. In general, it is preferred to irradiate all starch particles for this particular purpose as the physical chemical properties of the irradiated particles appears to be unexpectedly different from those of non-irradiated particles.

In view of the reliance (in the aforementioned '919 patent) upon the inherent well-known lubricity of a wax and/or a metal soap, in combination with the known spherical shape of atomized lubricants to provide highest flow rate and apparent density, it is particularly unexpected that particles of starch, a material which has no notable lubricity and low apparent density, could be combined with a known lubricant and yield a starch-modified lubricant, which not only has essentially the same physical properties of the lubricant without the starch, but also results in a blend with substantially similar apparent density and a compact with better green strength.

Though starch particles in the size range and amount specified above, by themselves, contribute no evident lubricity to a powder metal blend, they may be used in combination with any lubricant suitable for providing a compactable powder metal mixture, whether of low alloy steel or stainless steel, or prealloyed iron powder; preferably the ratio of cellulose fibers to lubricant is adjusted to provide a "modified lubricant" or "starchlube" which, blended with powder metal, yields a blend which has specifications of Hall apparent density and rate of flow dictated by the production requirements of a die for a chosen green part. A green part compacted with the starchlube provides higher green strength than another part compacted with the same lubricant (present in the same amount as the starchlube but without the fibers) under the same conditions, while meeting predetermined specifications of hardness and TRS for sintered parts. By "low alloy" powder is meant an iron-based powder which may contain from 0.5% to 5% by weight of graphite and from 0.1% to 25% of an element selected from the group consisting of Ni, Cu, Cr, Mo, Mn, P, Si, V and W. By "stainless steel" is meant a corrosion-resistant steel of a wide variety of compositions, but always containing a high percentage of chromium in the range from about 8% to 25%, typically from 0 to 12% Ni, and from 0 to about 0.5% C (carbon). By "prealloyed" is meant that the iron is melt-processed in such a manner as to have substantially homogeneously intermixed with it one or more alloying elements. Low alloy steel parts are typically made with much smaller amounts of other elements than either chromium or nickel, copper being used in a higher amount, up to about 5%, than Mn, Mo, Si, V, P and W which are typically used in an amount less than about 2%.

A ferrous metal powder may be selected from any of the foregoing iron-based powders. Typically, the ferrous metal powder is atomized powder or derived from a sponge iron with particles in a size range chosen to meet the specifications of the sintered final product.

Though any conventionally used waxy lubricant may be used, e.g. EBS, a preferred lubricant is a micronized polyolefin wax commercially available as a polymerized lower olefin oxide, or an oxidized polyolefin homopolymer or copolymer, the olefin having from 2 to 4 carbon atoms; most preferred is an oxidized micronized polyolefin homopolymer wax. Since less than 0.1% by weight of the non-lubricant does not contribute an appreciable advantage over the lubricant by itself, the amount of starchlube or (starchlube+cellulose fragments) used is preferably in the range from 0.25% to 1% by weight and the weight ratio of lubricant/starch in starchlube, or of lubricant/(starch+cellulose fragments) is in the range from about 1:2 to 10:1, preferably from 1:1 to 4:1.

A method is disclosed for making a homogeneous powder metal mixture comprising, mixing metal particles having an average equivalent particle diameter smaller than about 150 μm with additives including a modified lubricant present in an amount less than 2% by wt of the mixture, and optionally a binder, processing aids and additives conventionally used in the art, the modified lubricant consisting essentially of a particulate lubricant preferably having an avg. equiv. diam. smaller than 50 μm, in combination with starch particles having an avg. equiv. diam. smaller than 50 μm, optionally in combination with micronized cellulose fibers, for a time sufficient to yield specifications of (i) Hall apparent density numerically no smaller than 10% less than that obtained for the same powder metal mixture made with a conventional lubricant without the starch particles, and (ii) Hall flow rate which is preferably about 25-35 sec/50 g of mixture. Preferably, the Hall apparent density is numerically greater than that obtained for the same powder metal mixture made with a conventional lubricant without the starch particles.

In a powder metal mixture made with less than 2% by wt of a conventional lubricant, which mixture has an unacceptably low Hall flow rate of less than 25 sec/50 g, the addition of an equal part by weight but at least 0.1% by weight of particulate starch, or starch and micronized cellulose fibers, which, by itself provides a mixture of negligible lubricity, so that the non-lubricants and lubricant are together present in an amount less than 2% by wt of the mixture, yields a blend which not only has desirable Hall apparent density and flow rate but also results in higher green strength than if the starch particles were omitted. An unacceptable flow rate is one which results in an uneven fill of the die cavity. Optimum fill for most powder metal mixtures is in the range from 25-35 sec/50 g, slightly longer times, typically as much as 40 sec/50 g being acceptable if demand for speed of production is not too great.

A commercially usable blend of ferrous powder metal including less than 2% by wt of modified lubricant including from 0.1% to less than 1% by wt of starch particles in combination with from 0.1% to less than 1% by weight of a conventional, preferably polymeric lubricant has a Hall apparent density in the range from 2.7 to 3.5 g/cc, preferably from 2.9 to 3.3 g/cc and a Hall flow rate in the range from 25-35 sec/50 g, preferably from 29-33 sec/50 g. Blends which flow too slowly, or not at all, usually flow through a powder bin's delivery tube with no difficulty; such minor difficulty in filling a die cavity as may be encountered with some weight ratios of starch, may be overcome using an agitation means on the delivery tube, such as a mechanical or sonic vibrator. The slightly lower apparent density typically obtained with the novel modified lubricant is compensated for by deepening a die cavity conventionally used with a blend having a higher apparent density.

Starch particles as defined herein, in combination with a micronized synthetic wax such as a polyolefin wax particles having an equivalent diameter smaller than about 50 μm, are ingredients of a novel composition found not only to be a substitute for a metal soap such as zinc stearate or a fatty acid mono- or bis-amide, either wholly or in part, but also to provide higher green strength than is obtainable with an equivalent weight of lubricant without the starch particles. When molded green ferrous powder metal articles containing the starchlube are sintered in an oxygen-free atmosphere of a conventional sintering oven, the oven's flue does not require frequent cleaning as is the case with sintered zinc stearate-containing articles. The starch particles may be combined with an inorganic lubricant such as graphite, the function of the fibers being, in part, to replace a portion of the graphite otherwise used, or be combined with an organometal such as zinc stearate, the function of the fibers being, in part, to replace a portion of the organometal otherwise used.

DETAILED DESCRIPTION OF THE INVENTION

It is critical that starch particles in the aforementioned size range be used, and relatively less critical that the particles be gamma irradiated to modify their surfaces. The term "starch particles" refers to particles of starches derived from naturally occurring vegetable matter such as corn, potato, tapioca, rice, pea, wheat, and the like which yield particles in the aforementioned size range. It is believed that when a dosage in the range from 10 to 30 MegaRads is delivered to a mass of starch particles their surface structure is modified in such a way as to facilitate flow of a powder metal mixture when the irradiated starch is mixed with comparably small or smaller particles of conventional organic lubricants.

The starch is preferably contained in a fiber drum which is transported into a radiation room and held for successive periods of time until the desired dosage is acquired. Too low a dosage, for example, in the range from 2-6 MegaRads such as is typically used to kill bacteria, adversely affects the most desirable apparent density and flow rate of a powder metal mixture in which the irradiated starch particles are used; too high a dosage may degrade the color of the particles, if color is important, but does not substantially affect performance in combination with a lubricant; the optimum dosage for a particular fiber is arrived at by trial and error such as is customary under the circumstances.

Any conventionally used lubricant may be used in the powder metal mixture; particularly favored lubricants are those which imbue the blend with a Hall apparent density in the range from 2.7-3.5 g/cc and a Hall flow rate in the range from 29-35 sec/50 g. Commonly used lubricants are selected from the group consisting of metal soaps, and waxes particularly poly(lower $C_1$-$C_5$)olefin waxes and oxidized poly (lower)olefin homopolymers and copolymers, fatty acid bis-amides and fatty acid mono-amides. Preferred waxes are the Epolene® brand waxes designated E-10, 14, 15, 16, 17, 20, 43; G-3003 and G-3015; E-14, 20, 43; C-10, 13, 16, 17, 18; N-10, 11, 14, 15, 20, 21, 30, 34, 3; commercially available from Eastman Chemical Co.; and the Acumist® brand waxes designated A-6, 12, 18, 45; B-6, 9, 12, 18; C-5, 12, 18; D-5, 9; 1106, 1112, 1204, 1306, 3105, 3205; commercially available from Honeywell Corporation. The particular choice of wax will depend upon the physical characteristics of a particular metal powder, the conditions under which it is to be compacted and ejected, and the conditions under which the compacted part is to be sintered.

A blend containing a lubricant in combination with starch particles is conventionally prepared, requiring no additional processing steps. The ingredients are mixed until an essentially homogeneous blend is formed, and a die cavity in which a part is to be molded is filled with the blend; the blend is then compacted with a ram, matingly closely fitted into the die cavity, which exerts sufficient pressure, typically in the range from about 300 to 900 Mpa (43,500 psi or 43.5 Ksi or 21.75 Tsi, tons/in$^2$) to 1000 Mpa (130,500 psi or 130.5 Ksi, or 65.25 Tsi) to form a green part; the green part is then ejected from the mold with a peak ejection force insufficient to damage the integrity of the molded part, the force being in the range from about 453.6 to 2041.2 Kgf, kilogramsforce (1,000 to 4,500 lbf, pounds-force). The green part is then sintered in a sintering furnace in an inert atmosphere, typically nitrogen and/or hydrogen, under elevated temperature conditions high enough to volatilize the lubricant and some or all of the starch particles, and form a sintered metal part. The furnace encloses a belt moving at a speed sufficient to provide the desired time in the furnace's hot atmosphere, typically of 80% $N_2$/20% $H_2$, the belt speed being in the range from 2.54 cm (1") per min to 30.5 cm (12") per min in zones ranging from about 1000° F. to 2500° F.

Low alloy and prealloyed parts are typically not heat treated unless they contain enough graphite to warrant heat treating. Stainless steel parts are not heat treated. In most of the illustrative examples presented below, starch particles are used which are smaller than the powder metal particles to avoid having the dimensions of the starch interject an additional variable. The apparent density and flow rate of a blend containing only the starch particles and no lubricant were not measured because when a blend containing 0.75% by weight of starch particles was compacted with a pressure of 7030.77 Kg/cm$^2$ (50 TSI), the bar could not be ejected from the die cavity with an acceptable amount of force, indicating that starch provided no evident lubricity; therefore, a blend with the starch and no lubricant would not be usable. Further, only the essential ingredients are used to make each blend so as to focus the result-effectiveness of the starch particles. To focus the effect of starch particles in all blends, use of graphite is avoided unless the graphite is necessary to provide the desired properties of the sintered part.

EXAMPLES

The present invention is further illustrated by the following examples wherein the term parts refers to parts by weight unless otherwise indicated. All results are the average of a statistically significant number of identically performed tests, typically at least three. The following examples are not meant to be limiting, rather they are illustrative of only a few embodiments within the scope of the present invention.

Examples 1-11

Evaluation of Hall Apparent Density and Hall Flow Rate for MPIF F-0000 compositions using Hoeganaes Ancorsteel 1000B as the base iron and various lubricants, some in combination with starch particles, each lubricant or combination in an amount of 0.75% by weight (of the total mixture):

In the following Table 1, each sample is prepared as a 1 lb powder metal mixture ("blend") which was blended by thoroughly mixing the ingredients in a cylinder about 8 cm (3 ins) in diameter and about 30.5 cm (12") long. The cylinder is manually rolled for 30 sec, that is, it is rotated about its longitudinal central axis while being translated back and forth on a table; the cylinder is then tumbled, end over end, for 30 sec, that is, it is rotated end over end about its central lateral axis; then the cylinder is shaken by hand in plural axes for 30 sec. This procedure carried out over about 90 sec is then repeated once more to ensure substantial homogeneity. Each blend is then evaluated for Hall apparent density. Each of the powder mixtures with MPIF F-0000 (A1000B), listed below, is blended with 0.75% by weight of modified lubricant designated as a combination of conventional "lubricant" and "non-lubricant", the "non-lubricant"

being either micron-sized starch particles or micronized cellulose fibers, or both. The amount of each ingredient in each blend is given as percent by weight of the blended powder metal mixture.

"Allnat C" is an internal code designation for micronized cellulose fibers, specifically, cotton fibers.

"P-105" is an internal code designation for commercially available, micron-sized Acumist® A-12 polyolefin wax (lubricant) having a melting point in the range from about 137° C.-138° C. (279° F.-281° F.) which wax is used by itself in Blend 5.

In Blend #4, P-105 is used in combination with 0.375% starch and 0.187% Allnat C.

The starch particles used are Purity® 21C which were irradiated with a dosage of 15 MegaRads—other starch particles may have an apparent density in the range from about 2.8 g/cc to 3.2 g/cc. The optimum dosage for each type of starch will depend upon the source of the starch, its particle size and the reaction of its surface to different dosages of irradiation.

The remaining blends are designated consistent with the foregoing specifications.

Each of the blends made with the metal powder is then filled in a die cavity of a conventional mold and compacted under sufficient pressure to provide a green part. Compaction pressure and peak ejection pressures are generally within the range found acceptable in the commercial production of powder metal parts.

A sintered metal part is produced by mixing chosen lubricant and non-lubricant ingredients with the ferrous powder metal to be used to produce a compactable mixture; blending the ingredients to form a homogeneous mixture flowable in the desired range of flow rate, feeding the mixture into a die cavity; compacting the mixture to form a green article having a green density in the range from about 6.8 g/cc to 7.5 g/cc, depending upon the powder metal used; ejecting the green article; and, sintering it in a sintering oven under conditions suitable for producing the sintered metal part.

TABLE 1

| Blend No. | Lubricant Type % lubricant/% fibers | Hall Apparent Density g/cc | Hall Flow Rate sec/50 g |
|---|---|---|---|
| 1 | 0.375% Allnat C/0.375% starch | 2.79 | 30 |
| 2 | 0.50% Allnat C/0.25% starch | 2.77 | 30 |
| 3 | 0.25% Allnat C/0.25% starch & 0.25% P-105 | 3.04 | 24 |
| 4 | 0.187% Allnat C/0.375% starch & 0.187% P-105 | 3.04 | 25 |
| 5 | 0.75% P-105 | 2.98 | 29 |
| 6 | 0.75% starch | 2.92 | 25 |
| 7 | 0.56% P-105/0.19% fibers | 2.97 | 30 |
| 8 | 0.75% atomized Acrawax ® C | 3.10 | 31 |
| 9 | 0.75% zinc stearate | 3.32 | 25 |
| 10 | 0.375% starch/0.375% P-105 | 3.10 | 28 |
| 11 | 0.25% starch/0.5% P-105 | 3.04 | 30 |

It is evident from the foregoing data that all the blends have an acceptable flow rate in the range from about 27 to 36 sec/50 g. It is acknowledged that a lower flow rate may require vibrational delivery to accelerate the flow of the mixture. If the apparent density of atomized Acrawax C is taken as the standard, and a Hall apparent density of no less than 10% lower, that is, at least 2.69 g/cc be acceptable from a production point of view, then all the blends would be acceptable, though the density is desirably in the range from 2.9 to 3.3 g/cc to avoid deepening an existing mold.

It is also evident from the foregoing that, if P-105 is taken as the standard, then addition of modified lubricant in the amounts shown, increases the Hall apparent density, which is unexpected.

Each blend was then compacted at 7030.77 Kg/cm$^2$ or 50 TSI (tons/sq inch) into standard test bars, each 3.175 cm (1.25") long×1.27 cm (0.5") wide×0.635 cm (0.25") thick, to evaluate the effect of each lubricant on compressibility and green strength. Thereafter all the bars are sintered on a belt moving at about 12.7 cm/min (5"/min) in a conventional sintering furnace at through successive zones at temperatures of 649° C. (1200° F.), 760° C. (1400° F.), 1121° C. (2050° F.), and 1121° C. (2050° F.) in a 80% nitrogen/20% hydrogen atmosphere; and properties of the sintered bars are evaluated.

It will be appreciated that the amount of modified lubricant used, as well as the choice of the ratio of lubricant to non-lubricant, will depend upon the particular powder metal mixture being compacted, and the specifications (to be met) of the sintered part. Too high or too low a combined amount, or ratio of one component relative to the other, will result in a blend which is outside the desirable parameters of apparent density and flow rate. In general, when the modified lubricant is present in amount less than 0.5% or more than 1.5% by weight, the blend is not readily usable in a production run; therefore the amount is preferably no more than 1.5% by weight, and more preferably no more than 1% by weight.

The bars made with the blends numerically identified in Table 1 above are evaluated for green density, green strength, and the peak ejection pressure required to eject the bars from the die cavity. The bars are then sintered in a sintering furnace equipped with a belt moving at 8.9 cm (3.5") per sec through zones having successively higher temperatures of to provide the desired time in the furnace's hot atmosphere of 97% N$_2$/3% H$_2$, the belt speed being in the range from 2.54 cm (1")/min to 30.5 cm (12")/min through four main temperature zones at 648.9° C. (1200° F.); 760° C. (1400° F.); 1121° C. (2050° F.); and 1121° C. (2050° F.). The length of each zone is approximately 3 meters (7' 7").

The sintered density, sintered TRS, sintered apparent Rockwell F hardness (HRF), and sintered dimensional conformance (DC) of at least three samples are measured and averaged.

The results are presented in the following Table 2:

TABLE 2

| Blend No. | Gr. Density g/cc @ 7$^+$K Kg/cm$^2$ | Gr. Strength MPa (psi) @ 7$^+$K Kg/cm$^2$ | Peak Ejec'n Pressure Kgf (lbf) @ 7$^+$K Kg/cm$^2$ | Sintered Density, g/cc | Sintered TRS MPa (Ksi) | Sintered Apparent Hardness H RF | Sintered DC, % from Die Size |
|---|---|---|---|---|---|---|---|
| 1 | 7.06 | 28.8 (4185) | 2743 (6046) | 7.11 | 559 (81.2) | 72 | 0.17 |
| 2 | 7.15 | 30.67 (4452) | 3262 (7191) | 7.11 | 588 (85.3) | 73 | 0.15 |

TABLE 2-continued

| Blend No. | Gr. Density g/cc @ 7⁺K Kg/cm² | Gr. Strength MPa (psi) @ 7⁺K Kg/cm² | Peak Ejec'n Pressure Kgf (lbf) @ 7⁺K Kg/cm² | Sintered Density, g/cc | Sintered TRS MPa (Ksi) | Sintered Apparent Hardness H RF | Sintered DC, % from Die Size |
|---|---|---|---|---|---|---|---|
| 3 | 7.10 | 27.31 (3964) | 1383 (3048) | 7.15 | 582 (84.5) | 72 | 0.16 |
| 4 | 7.06 | 25.53 (3706) | 1456 (3210) | 7.09 | 548 (79.6) | 71 | 0.16 |
| 5 | 7.13 | 25.45 (3694) | 1267 (2793) | 7.11 | 455 (66.1) | 59 | 0.26 |
| 6 | 7.01 | 31.15 (4521) | 3195 (7042) | 7.07 | 589 (85.5) | 70 | 0.22 |
| 7 | 7.13 | 24.07 (3493) | 1577 (3476) | 7.12 | 599 (87.) | 73 | 0.15 |
| 8 | 7.16 | 17.2 (2496) | 1247 (2749) | 7.16 | 508 (73.7) | 65 | 0.18 |
| 9 | 7.12 | 14.65 (2127) | 1196 (2636) | 7.11 | 508 (73.7) | 61 | 0.29 |
| 10 | 7.04 | 28.9 (4200) | 1543 (3401) | 7.08 | 560 (81.3) | 69 | 0.17 |
| 11 | 7.10 | 29.53 (4287) | 1409 (3106) | 7.07 | 549 (79.7) | 67 | 0.12 |

In the above Table 7⁺K Kg/cm² refers to 7,030.8 Kg/cm² pressure = 50 tons/in² (TSI), and, Mpa refers to megapascals where 1 Mpa = 1000 KPa It is evident from the foregoing results that the green strengths of Blends #1 through #7 and #s 10 & 11 are about double the green strengths of both Blends #s 8 (Acrawax C) & 9 (zinc stearate). Though peak ejection pressures for Blends #1, 2 & 6 are double those for Blends #s 8 & 9, the peak ejection pressures, that is, the force required to initiate movement of a molded part out of the die cavity (measured with a load cell) for Blends #s 10 & 11, are only about 25% higher. All ejection pressures are within an acceptable range.

It is also evident that the transverse rupture strength (TRS) and apparent Rockwell F hardness of all the bars made from the novel sintered blends are higher than those for sintered bars made with zinc stearate, Acrawax and Acumist. Moreover, the novel sintered bars have the best dimensional conformance (DC), that is, the least distortion.

Having thus provided a general disclosure of the relevant subject matter and described the novel modified lubricant and powder metal mixture in detail, and illustrated the invention with a specific embodiment of the best mode of making and using the invention, it is to be understood that no undue restrictions are to be imposed by reason of the specific embodiment illustrated and described, and particularly, that the invention is not restricted to a slavish adherence to the details set forth herein.

What is claimed is:

1. A powder metal mixture comprising a ferrous metal powder and a modified lubricant, starchlube, consisting essentially of (a) a lubricant powder and (b) starch particles having an average equivalent diameter less than 150 μm, the modified lubricant being present in an amount less than 2% by weight of the composition, the mixture having (i) a Hall apparent density numerically no smaller than 10% less than that obtained for the same powder metal mixture made with the lubricant powder without the starch particles, and (ii) a Hall flow rate which is in the range from about 25-40 sec/50 g of mixture.

2. The mixture of claim 1 wherein the starch particles have an average equivalent diameter less than 50 μm, and the lubricant powder is selected from the group consisting of fatty acid monoamides, fatty acid bisamides, metal soaps and polyolefin waxes.

3. The mixture of claim 1 wherein about 90% by wt of the starch particles have an avg. equiv. dia. in the range from 5 to 50 μm; from 5 to 40% by wt have an avg. equiv. dia. in the range from 2 to 20 μm; and the starch has a Hall apparent density in the range from 2.8 to 3.2 g/cc, and the Hall flow rate of the mixture is in the range from about 25-35 sec/50 g of mixture.

4. The mixture of claim 1 including fragmented cellulose fibers having an average length less than 150 μm and a diameter in the range from about 1μ to 20μ, present in an amount no more than the starch particles.

5. The mixture of claim 4 wherein the modified lubricants starchlube, is preferably in the range from 0.25% to 1% by weight and the weight ratio of lubricant/starch in starchlube, and, of lubricant/(starch+cellulose fragments) if present, is in the range from about 1:2 to 10:1.

6. The mixture of claim 1 wherein the starch particles are irradiated with from 10-30 MegaRads of gamma radiation.

7. The mixture of claim 6 including fragmented cellulose fibers having an average length less than 150 μm and a diameter in the range from about 1μ to 20μ, present in an amount no more than the starch particles, and the starch particles are irradiated with from about 15 MegaRads of gamma radiation.

8. The mixture of claim 7 wherein the fragmented cellulose fibers have been exposed to electron beam radiation to receive a dosage in the range from about 30 to 100 Mega-Rads.

9. In a powder ferrous metal mixture including a lubricant, the mixture having a Hall flow rate in the range from about 25-40 sec/50 g of mixture, the improvement comprising a modified lubricant consisting essentially of (i) a lubricant powder and (ii) starch particles having an average equivalent diameter less than 150 μm present in an amount from about 0.25% to less than 0.75% by weight of the mixture, and (iii) fragmented cellulose fibers having an average length less than 150 μm and a diameter in the range from about 1μ to 20μ, present in an amount from 0% to less than 0.75% by weight of the mixture, but no more than the starch present, the modified lubricant being present in an amount less than 1.5% by weight of the composition, the mixture having a Hall apparent density numerically no smaller than 10% less than that obtained for the same powder metal mixture made with the lubricant powder without the starch particles, the weight ratio of lubricant/starch in starchlube, and, of lubricant/(starch+cellulose fragments), if present, is in the range from about 1:2 to 10:1.

10. The mixture of claim 9 wherein the starch particles are irradiated with from 10-30 MegaRads of gamma radiation, and the fragmented cellulose fibers have been exposed to electron beam radiation to receive a dosage in the range from about 30 to 100 MegaRads, and the Hall flow rate is in the range from about 25-35 sec/50 g of mixture.

11. A method for making a homogeneous ferrous powder metal mixture comprising,
  combining metal particles having an average particle diameter smaller than about 150 μm with a modified lubricant consisting essentially of (a) lubricant powder and (b) starch particles having an average equivalent diameter less than 150 μm, the modified lubricant being present in an amount less than 2% by weight of the composition, the mixture having (i) a Hall apparent density numerically no smaller than 10% less than that obtained for the same powder metal mixture made with the lubricant powder without the starch particles, and (ii) a Hall flow rate which is in the range from about 25-40 sec/50 g of mixture, and,
  compacting the mixture in a die to form a compacted green article.

12. The method of claim 11 wherein the Hall apparent density is greater than that obtained for the same powder metal mixture made with the lubricant powder without the starch particles, and the Hall flow rate is in the range from about 25-35 sec/50 g of mixture.

13. A modified lubricant adapted for use in a powder metal article, the modified lubricant consisting essentially of a lubricant selected from the group consisting of an inorganic compound, an organometal compound, and a wax, the lubricant having an average particle diameter smaller than 50 μm, in combination with starch particles, wherein about 90% by wt of the starch particles have an avg. equiv. dia. in the range from 5 to 50 μm; from 5 to 40% by wt have an avg. equiv. dia. in the range from 2 to 20 μm; and the starch has a Hall apparent density in the range from 2.8 to 3.2 g/cc.

14. The modified lubricant of claim 13 wherein the starch particles are irradiated with from 10-30 MegaRads of gamma radiation.

15. The modified lubricant of claim 14 including fragmented cellulose fibers having an average length less than 150 μm and a diameter in the range from about 1μ to 20μ, present in an amount no more than the starch particles.

16. The modified lubricant of claim 15 wherein the fragmented cellulose fibers have been exposed to electron beam radiation to receive a dosage in the range from about 30 to 100 MegaRads.

* * * * *